US00PP15016P2

(12) United States Plant Patent
Farrow

(10) Patent No.: US PP15,016 P2
(45) Date of Patent: Jul. 13, 2004

(54) JAPANESE SPIREA PLANT NAMED 'LEMONDROP'

(50) Latin Name: *Spiraea japonical*
Varietal Denomination: Lemondrop

(75) Inventor: Michael Farrow, Earlville, MD (US)

(73) Assignee: CP (Delaware), Inc., Wilmington, DE (US)

( * ) Notice: Subject to any disclaimer, the term of this patent is extended or adjusted under 35 U.S.C. 154(b) by 101 days.

(21) Appl. No.: 10/345,331

(22) Filed: Jan. 16, 2003

Related U.S. Application Data

(63) Continuation of application No. 09/874,299, filed on Jun. 6, 2001, now abandoned.

(51) Int. Cl.[7] ..... A01H 5/00

(52) U.S. Cl. ..... Plt./226

(58) Field of Search ..... Plt./226

*Primary Examiner*—Kent Bell
(74) *Attorney, Agent, or Firm*—Burns, Doane, Swecker & Mathis, L.L.P.

(57) ABSTRACT

A new variety of *Spiraea japonica* plant is provided that is well suited for growing as attractive ornamentation. The new variety exhibits a dwarf mounding growth habit. Attractive mauve-pink blooms commonly are formed from May to October. Yellow-Green foliage is displayed that is more yellow when grown in full sun. The available Spirea choices are expanded.

4 Drawing Sheets

Botanical/commercial classification: *Spiraea japonica*/ Japanese Spirea.

Varietal denomination: cv. 'Lemondrop'.

This Application is a Continuation of application Ser. No. 09/874,299, filed Jun. 6, 2001 (now abandoned).

SUMMARY OF THE INVENTION

The new *Spiraea japonica* plant of the present invention was discovered during July, 1998 at Holly Hill Farms, Earlville, Md., U.S.A., while growing among plants of the 'Little Princess' variety (non-patented in the United States). Such plant is believed to be a whole plant mutation of unknown causation of the 'Little Princess' variety. The new plant has been carefully preserved and studied in view of its distinctive combination of characteristics. Had the new variety of the present invention not been discovered and preserved, it would have been lost to mankind.

It was found that the new *Spiraea japonica* plant of the present invention displays the following combination of characteristics:

(a) exhibits a dwarf mounding growth habit, (b) forms attractive mauve-pink blooms, and (c) forms yellow-green foliage that is more yellow when grown in full sun.

The new variety well meets the needs of the horticultural industry and is particularly well suited for use as a border planting, foundation planting, or mass planting. It also can be grown to advantage in rock gardens.

Good winter hardiness has been displayed when plants were grown during the winter above ground in containers at West Grove, Pa., U.S.A., and in the ground at Earlville, Md., U.S.A.

Plants of the new variety can be readily distinguished from those of the 'Little Princess' variety (non-patented in the United States). More specifically, the new variety displays a dwarf stature unlike the 'Little Princess' variety, displays mauve-pink blooms unlike the pink blooms of the 'Little Princess' variety, and displays bright yellow-green foliage that is more yellow in full sun unlike the green foliage of the 'Little Princess' variety.

The rooting of cuttings has been used to asexually propagate the new variety at Earlville, Md., U.S.A., and at West Grove, Pa., U.S.A. It has been found that the characteristics of the new variety are stable and are reliably transmitted from one generation to another.

The new variety has been named 'Lemondrop'.

BRIEF DESCRIPTION OF THE PHOTOGRAPHS

The accompanying photographs show plants of the new variety in color as nearly true as it is reasonably possible to make the same in color illustrations of this nature. The plants had been propagated from rooted cuttings.

DETAILED DESCRIPTION

Figure 1:
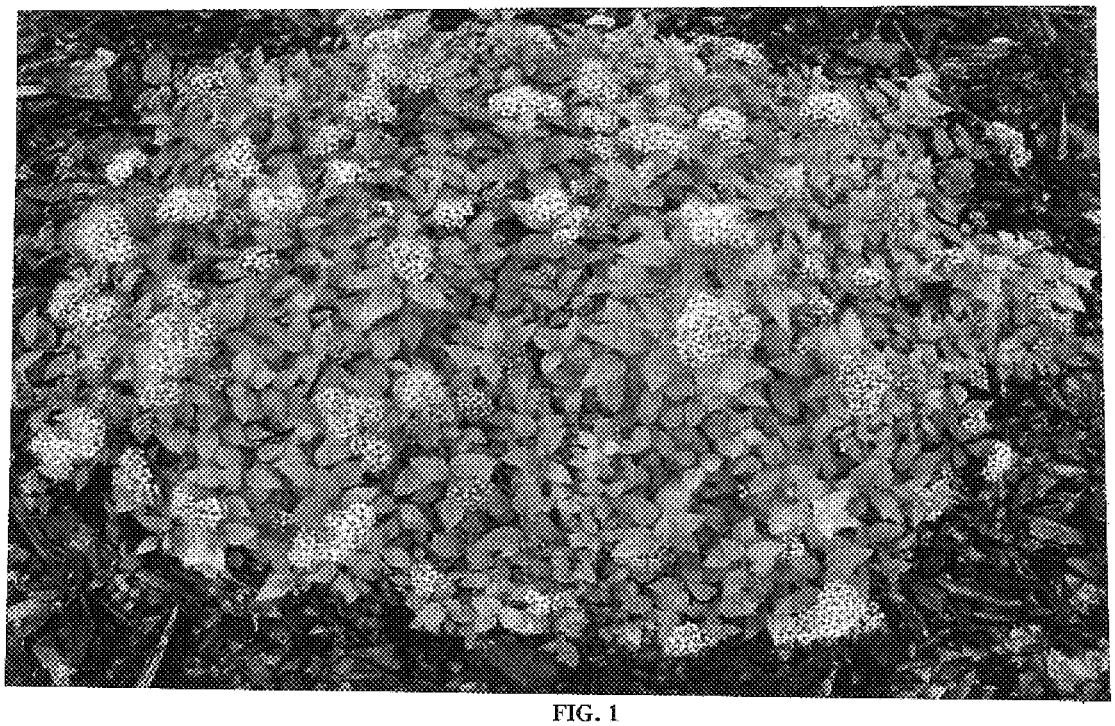
FIG. 1 illustrates an overall view of an approximately four year-old plant of the new variety with blooms during June 2002 and growing in partial sun at Earlville, Md., U.S.A. The attractive mauve-pink blooms and yellow-green foliage are shown.

The following is a detailed description of the new variety while observing plants of approximately two years of age during May while being grown outdoors on their own roots at West Grove, Pa., U.S.A., except as otherwise indicated. The chart used in the identification of color is The R.H.S. Colour Chart of The Royal Horticultural Society, London, England. Common color terms are to be accorded their customary dictionary significance.

Botanical classification: *Spiraea japonica,* cv. 'Lemondrop'.

*Parent.*—*Spiraea japonica,* cv. 'Little Princess'.

Plant:

*Type.*—Perennial shrub, groundcover.

*Growth habit.*—Dwarf mounding.

*Height.*—Approximately 6 to 8 cm. This can be compared to a height of approximately 15 to 20 cm for the 'Little Princess' variety.

*Width.*—Approximately 10 to 18 cm. This can be compared to width of approximately 20 to 25 cm for the 'Little Princess' variety.

*Stems.*—Current season growth information is provided for a plant of approximately five years of age growing in the ground during June 2003 at Earlville, Md., U.S.A. Length: Approximately 15 to 25 cm (average approximately 19 cm) for vigorous plagiotropic shoots, and approximately 3 to 8 cm (average 5 cm) for slower growing plagiotropic shoots. Diameter: Near 2 mm. Internode Length: Approximately 6 to 10.5 mm (average approximately 7.6 mm) on vigorous flowering shoots, and approximately 2.5 to 4 mm (average approximately 3.4 mm) on smaller slower growing secondary shoots. Color: On young still elongating stems close to Yellow-Green Group 145B with overtones of Greyed-Yellow Group 160A. On maturing stems formed earlier in the season primarily near and through Greyed-Orange Group 177B with areas near and through Greyed-Orange Group 165A and 177A with highlights near and through Greyed-Orange Group 164A and 165A.

Foliage:

*Arrangement.*—Alternate.

*Configuration.*—Ranges from narrowly elliptic to narrowly ovate to ovate.

*Apex.*—Narrowly acute.

*Base.*—Broadly to narrowly cuneate.

*Length.*—Variable from 5 mm to 3.5 cm.

*Width.*—Variable from 3 mm to 1.5 cm.

*General aspect.*—Dense, small and bright yellow when young foliage is present.

*Color.*—The intensity of the leaf coloration varies with exposure to sunlight with more yellow and less green being apparent when the plant is grown in full sunlight. Young Foliage: On the upper surface depending upon light exposure near Yellow-Green Group 145A and 145B and shades gradually and continuously near on through Yellow-Green Group 149A, 149B, 150A and 151D, approaching Yellow Group 9B and 10B depending upon exposure to bright sun, and on the lower surface depending on light exposure Green Group 142C and shades gradually and continuously near and through Yellow-Green Group 149C, 149D, 150B, 150C, 154C and 154D, approaching Yellow Group 10A and 10B depending upon exposure to bright sun. Mature Foliage: On the upper surface depending upon light exposure near Green Group 143A and 143B and shades gradually and continuously near and through Yellow-Green Group 145A, 149A, 149B, 150A, and 151D, approaching Yellow Group 9B and 10B depending upon exposure to bright sun, and on the lower surface depending upon light exposure near Green Group 138B and Yellow-Green Group 143A and 143C, and occasionally shades towards the lighter shades such as Yellow-Green Group 149A.

*Margin.*—Serrate in the upper ⅔rds of the leaf, more rarely only in the upper ½, and commonly entire along the lower ⅓rd of the leaf.

*Petiole.*—Approximately 2 mm in length on average, approximately 0.8 mm in diameter on vigorous growing primary shoots, and approximately 0.4 to 0.6 mm (average approximately 0.5 mm) in diameter on smaller secondary stems, and the color commonly is near and shades through Yellow-Green Group 145A and 145B, and Yellow-Green Group 144C.

Inflorescence:

*Arrangement.*—Compound corymbs on stems of the current year's growth. The inflorescence may contain as few as 5 up to as many as approximately 75 flowers.

*Bud shape.*—Globose to sub-globose.

*Bud size.*—Approximately 1.8 to 1.9 mm in length, and approximately 1.7 to 1.9 mm (average approximately 1.8 mm) in diameter.

*Bud texture.*—Commonly lightly covered with silvery-white villous to pilose hairs that are somewhat appressed and average approximately 0.3 mm in length.

*Bud color.*—Green Group 143D with Greyed-Red Group 182A and 182B at the tips.

Figure 2:
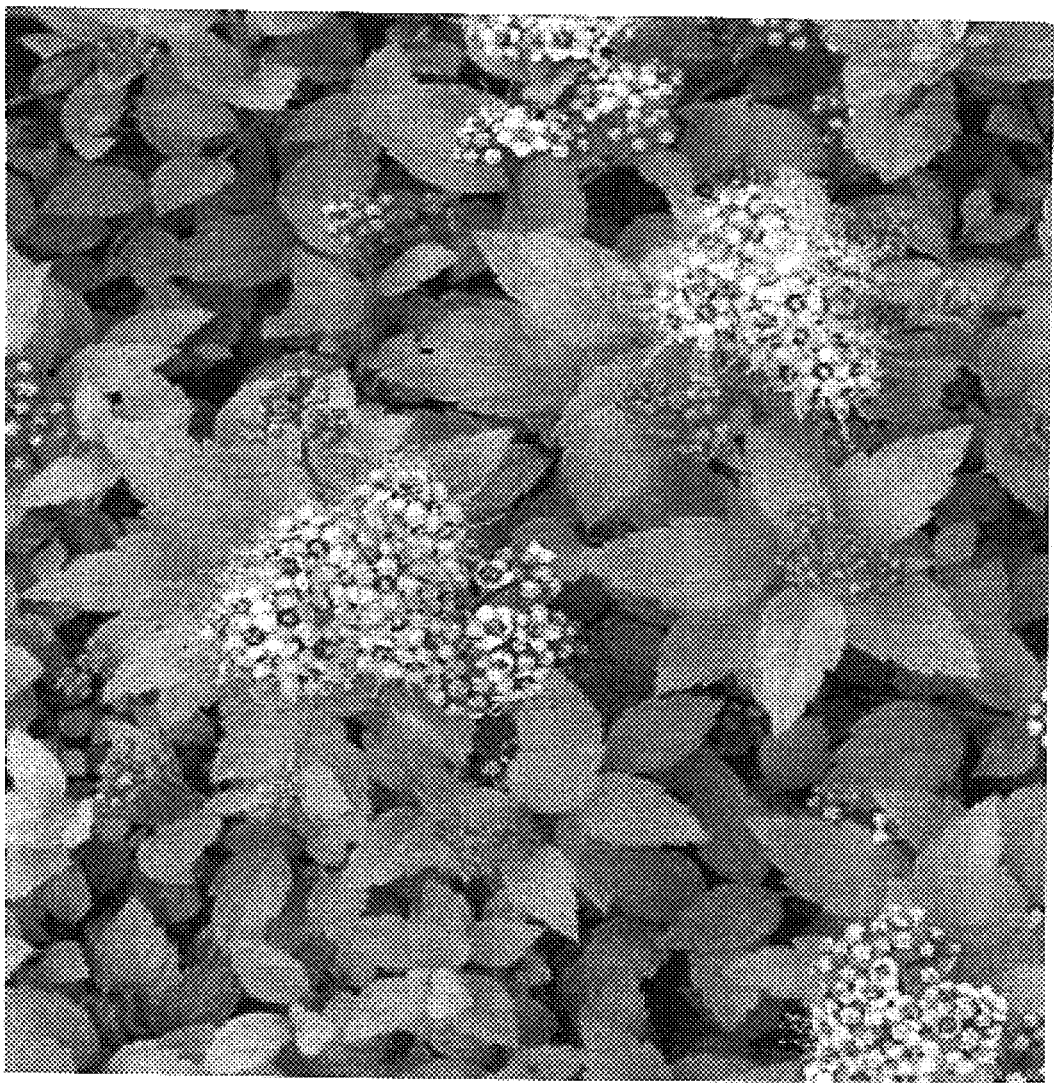
FIG. 2 illustrates a closer view of typical blossoms and foliage of an approximately five year-old plant of the new variety during June 2003 while growing in partial sun at Earlville, Md., U.S.A.
Figure 3:
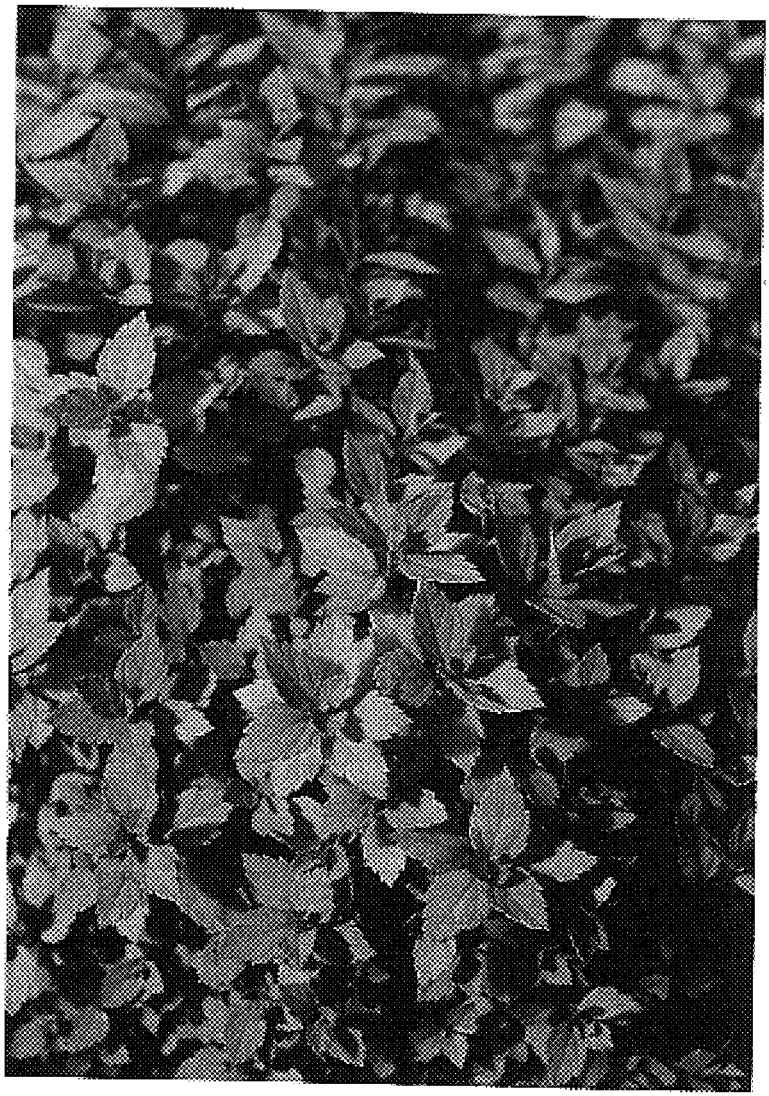
FIG. 3 illustrates during June 2001 the typical bright yellow young foliage of the new variety that includes shades of light green as the foliage begins to mature. The plant was approximately two years of age and was growing in a container in full sun at West Grove, Pa., U.S.A.
Figure 4:
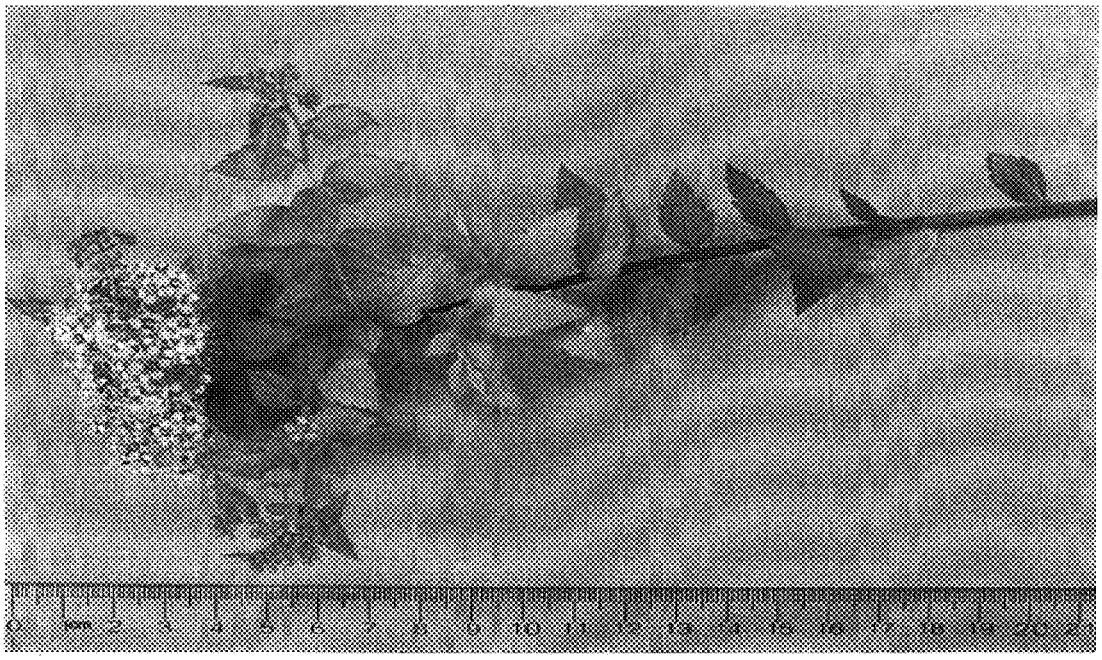
FIG. 4 illustrates a close view of a flowering stem with dimensions in centimeters being included at the bottom. The plant was approximately five years of age and was growing in partial sun at Earlville, Md., U.S.A.

*Flower color.*—Mauve-pink as illustrated in FIGS. 1 and 2.

*Flower diameter.*—Approximately 5 mm with no appreciable depth when fully open in a flattened configuration.

*Type.*—Perfect (bisexual), polypetalous (i.e., the petals are completely separate).

*Petal shape.*—Suborbicular to broadly elliptical.

*Petal apex.*—Broadly obtuse to rounded.

*Petal base.*—Truncate.

*Petal margin.*—Entire and slightly undulate.

*Petal length.*—Approximately 1.8 mm on average when flower is fully open.

*Petal width.*—Approximately 2 mm on average when flower is fully open.

*Petal color.*—On both surfaces near Purple Group 75C to 75D with shading to near and through Purple Group 77B at the base.

*Petal number.*—Five.

*Pistils.*—Five in number and approximately 1.5 mm in length.

*Stigma.*—Approximately 0.2 mm in size.

*Stamen.*—Approximately 25 or more in number.

*Filaments.*—Approximately 0.3 to 0.35 mm in length.

*Pollen.*—Present and near Yellow-White Group 158D in coloration.

*Habit.*—Commonly blooms continuously from May to October. This can be compared to the 'Little Princess' variety which commonly initiates blooming in mid-spring and blooms for approximately 5 weeks.

*Peduncle.*—Approximately 3 mm in length, approximately 0.5 mm in diameter, and the coloration is near and shading through Yellow-Green Group 147A, 147B, and 148B with a reddish tinge near Greyed-Purple Group 187B.

*Sepals.*—Five in number, obturbinatus, possess an acute apex, the margin is entire, approximately 1.1 mm in length from the apex to the point where the sepals unite, approximately 1.3 mm in width at the widest part where the sepals unite at the base, and on both surfaces the coloration is near and through Green Group 138A towards the apex and near and through Green Group 138D and shading near and through Greyed-Green Group 193A towards the base.

*Fruit/seed.*—During observations to date no fruit and seed production has been noted.

Development:

*Propagation.*—Propagates well through the rooting of cuttings.

*Disease resistance.*—Typical of Spirea.

*Winter hardiness.*—Good, has over-wintered well in containers at West Grove, Pa., U.S.A., and in the ground at Earlville, Md., U.S.A. Performs well in U.S.D.A. Hardiness Zone No. 6.

Plants of the 'Lemondrop' cultivar have not been observed under all possible environmental conditions to date. Thus, the phenotypic expression may be found to vary somewhat with different light intensity and duration, cultural, and environmental conditions.

I claim:

1. A new and distinct variety of *Spiraea japonica* plant having the following combination of characteristics:

(a) exhibits a dwarf mounding growth habit, (b) forms attractive mauve-pink blooms, and (c) forms yellow-green foliage that is more yellow when grown in full sun;

substantially as illustrated and described.

* * * * *